(12) United States Patent
Hammer et al.

(10) Patent No.: US 6,813,019 B2
(45) Date of Patent: Nov. 2, 2004

(54) METHOD AND APPARATUS FOR SPECTROCHEMICAL ANALYSIS

(75) Inventors: Michael R. Hammer, Sassafras (AU);
Philip V. Wilson, Mount Waverley (AU); Mark R. Williams, Box Hill (AU); Dower C. Bricker, Selby (AU); Martin K. Masters, Rowville (AU); Stewart R. Campbell, Forest Hill (AU); Peter G. Layton, Hampton Park (AU)

(73) Assignee: Varian Australia PTY LTD, Mulgrave (AU)

( * ) Notice: Subject to any disclaimer, the term of this patent is extended or adjusted under 35 U.S.C. 154(b) by 301 days.

(21) Appl. No.: 09/958,458
(22) PCT Filed: Feb. 15, 2001
(86) PCT No.: PCT/AU01/00148
§ 371 (c)(1),
(2), (4) Date: Oct. 5, 2001
(87) PCT Pub. No.: WO01/61292
PCT Pub. Date: Aug. 23, 2001

(65) Prior Publication Data
US 2002/0180970 A1 Dec. 5, 2002

(30) Foreign Application Priority Data

Feb. 15, 2000 (AU) ............................................. PQ5653
Aug. 8, 2000 (AU) ............................................. PQ9273
Sep. 7, 2000 (AU) ............................................. PQ9960

(51) Int. Cl.$^7$ ................................................. G01J 3/28
(52) U.S. Cl. ...................................... 356/330; 356/326
(58) Field of Search ................................. 356/326, 330, 356/436, 437, 440; 422/82.09, 82.05; 436/164, 171

(56) References Cited

U.S. PATENT DOCUMENTS

| | | | | |
|---|---|---|---|---|
| 5,412,468 A | * | 5/1995 | Lundberg et al. | 356/326 |
| 5,528,363 A | * | 6/1996 | Fachinger et al. | 356/326 |
| 5,596,407 A | * | 1/1997 | Zander et al. | 356/328 |
| 5,689,333 A | * | 11/1997 | Batchelder et al. | 356/301 |
| 5,784,158 A | * | 7/1998 | Stanco et al. | 356/326 |

* cited by examiner

Primary Examiner—Frank G. Font
Assistant Examiner—Willie Davis
(74) Attorney, Agent, or Firm—Edward H. Berkowitz; Bella Fishman

(57) ABSTRACT

A method and apparatus for the spectrochemical analysis of a sample in which a solid state array detector (82) is used to detect radiation (62) of spectrochemical interest. The invention involves the use of a shutter (72) adjacent the entrance aperture (70) of a polychromator (74–80) to expose the detector (82) to the radiation (62) for varying lengths of time whereby for short duration exposure times charge accumulation in elements (i.e. pixels) of the detector (82) due to high intensity components of the radiation is limited and for longer exposure times charge accumulation in elements (pixels) of the detector (82) due to feeble intesity components of radiation (62) is increased. This ensures that each reading of the detector (82) includes at least one exposure in which the amount of charge accumulated at each wavelength of interest is neither too little or too great. The problems of feeble radiation components not being accurately measurable and of high intensity radiation components exceeding the charge carrying capacity of elements (pixels) of the detector (82) are thereby able to be avoided. An attenuator (90) may be placed between the radiation source (60) and the detector (82) to permit longer exposure times to be used for very high intensity radiation.

12 Claims, 3 Drawing Sheets

METHOD AND APPARATUS FOR SPECTROCHEMICAL ANALYSIS

FIELD OF THE INVENTION

The present invention relates to a method and apparatus for the spectrochemical analysis of a sample in which a solid-state array detector is used to detect radiation of spectrochemical interest. In particular, the method and apparatus relate to utilisation of the solid state array detector.

Throughout this specification, the terms "light" and "radiation" have been used interchangeably.

BACKGROUND

It is known that chemical analysis of samples can be accomplished by a variety of spectroscopy-based techniques. For example, the amount of various chemical elements in a sample can be ascertained by optical emission spectrometry or by atomic absorption spectrophotometry. The concentration of various chemical species in a sample can be ascertained by ultraviolet—visible absorption spectrometry or infrared absorption spectrophotometry, or by ultraviolet-visible fluorescence spectrophotometry. These are only a few examples of spectroscopy-based chemical analysis techniques.

Apparatus for spectroscopy-based chemical analysis typically operates by measuring the intensity of light either as a function of wavelength or at one or more specific wavelengths. This may be done with a monochromator and a single detector collecting intensity data for each wavelength of interest in a serial fashion, but it is also possible to collect light intensity data for more than one wavelength simultaneously. Because of the greater time efficiency offered by simultaneous measurement, this approach is increasingly favoured for practical applications.

Modern simultaneous spectroscopic measurement apparatus typically includes an optical polychromator together with a solid state electronic detector device incorporating an array of optical sensor elements. The detector can be, for example, a charge-transfer device such as a charge-injection device (CID) or a charge-coupled device (CCD). A polychromator that is able to disperse the light in two dimensions (for example an echelle polychromator) can be employed, in which case a 2-dimensional array of optical sensor elements can be used with advantage as a detector. Alternatively a polychromator that provides dispersion in one dimension only (such as a single-grating-based polychromator) can be utilised, and a linear array detector used. The 2-dimensional approach offers better wavelength resolution for a given wavelength range and so is favoured for chemical analysis applications, particularly for elemental analysis by optical emission spectrometry. Compared to linear detectors, such two-dimensional arrays are more compact. The need for several detectors to cover the focal plane of the spectrometer can be avoided by the use of an appropriate two-dimensional array detector.

Elemental analysis typically involves operation at optical wavelengths extending from the visible to the far ultraviolet, which places limitations on the types of detectors that can be used. Primarily, the detector must be efficiently responsive to radiation across this range of wavelengths. Solid-state detectors of various types are known to be suitable for this application, for example charge transfer devices, both CIDs and CCDs, are known to be useful. Such devices are described, for example, in the book 'Charge Transfer Devices in Spectroscopy', J. V. Sweedler, K. L. Ratslaff and M. B. Denton, eds., VCH Publishers, Inc., New York, 1994. ISBN 1-56081-060-2. CCDs are discussed in 'Scientific Charge-Coupled Devices', J. R. Janesick, SPIE Press , Bellingham, Wash., 2001, ISBN0-8194-3698-4.

A specific example of such a detector is the CCD detector disclosed by Zander et al. in U.S. Pat. No. 5,596,407. This has a number of optically sensitive sites, generally referred to as pixels, that are distributed in a precise geometric arrangement over the surface of the detector to map accurately the optical image from the polychromator. Each optically sensitive site or pixel is capable of converting the energy of incoming light to free electrons, which are stored at the optically active site. The number of electrons, and thus the total charge, accumulated within each pixel will depend on the light intensity incident on that pixel and the time for which the pixel is exposed to said light, said time being usually referred to as the integration time.

Measuring the optical intensity therefore involves determining the amount of charge built up over a known integration period. In order to do this it is necessary first to collect the charge and then to transfer the charge accumulated at each pixel to appropriate readout electronics. Two principal ways of carrying out this process are available. The first, used in the detector disclosed by Zander et al. in U.S. Pat. No. 5,596,407, duplicates each optically active pixel with an optically inactive pixel. The first step in the readout process is a parallel transfer operation that transfers the charge from each row of active pixels to the corresponding row of inactive pixels so that these inactive pixels are used as the shift register nodes. The charge is then stepped through one optically inactive pixel to the next to readout electronics at the end of the row. The second approach uses the optically active pixels themselves as shift register nodes, so that with each move operation the charge on every pixel moves to the next pixel along, with the charge of the first pixel moving to the readout circuit.

Both approaches have their attendant advantages and disadvantages. The second approach has the advantage that most of the surface area of the CCD can be covered by active pixels, thus maximising the light sensitivity of the whole device. It also avoids the need for any secondary structure. That is, this approach provides more efficient utilisation of available light in spectroscopic applications. It also permits the use of relatively inexpensive, off-the-shelf detectors, or of custom-designed detectors that can be fabricated relatively inexpensively using the same technology as that used for the off-the-shelf detectors.

The disadvantage of the second approach is that the pixels continue to accumulate electrons generated by any incoming light during the readout process. As a consequence, as the charge from one pixel moves through other pixels on its way to the readout circuitry, it accumulates additional charge, the amount of which depends on the light intensity incident at each of those other pixels and the speed of charge transfer. This has the effect of smearing the resultant image data, which is unacceptable in a spectroscopy application.

The smearing problem does not occur with the first approach, since the readout occurs through optically inactive pixels. However this advantage is at the expense of the need for a secondary structure and a reduced overall light sensitivity, due to the loss of that proportion of the detector's surface area that is taken up by the inactive pixels. Additionally, detectors of this type have to be custom-designed and custom-built, and are consequently expensive.

In spectrochemical applications it is common for a sample to emit extremely intense radiation at certain wavelengths and to emit extremely feeble radiation at other wavelengths, depending on the amount of specific chemical elements present in that sample. To extract the required chemical information it is often necessary to measure both extremely feeble and extremely intense radiation from the same sample. This presents problems in that if the detector is exposed to radiation for a sufficient time to generate accurately measurable charge from extremely feeble radiation, those parts of the detector that are exposed to extremely intense radiation will have accumulated excessive charge. Charge accumulation is excessive when it exceeds the capacity of the device to store it. Not only is such excessive charge useless for measurement of the intensity of the radiation that generated it, but it can also spill over into adjacent regions of the detector and impede or prevent the correct functioning of those regions. Such a process is known as 'blooming'. Conversely, if the detector is exposed for the short period of time appropriate for the measurement of extremely intense radiation, those regions of the detector that are exposed only to feeble radiation will not accumulate sufficient charge to allow accurate measurement.

SUMMARY OF THE INVENTION

According to a first aspect of the invention, there is provided a method for spectrochemical analysis of a sample comprising (i) interacting a representative portion of the sample and a spectroscopic radiation source to produce spectral radiation of the sample, (ii) measuring the intensity of the spectral radiation as a function of wavelength by passing the spectral radiation through a polychromator onto a multielement solid state detector and reading a plurality of elements of the detector, including (iii) exposing the detector to the spectral radiation for a plurality of exposure times of varying duration whereby for short exposure times charge accumulation in elements of the detector due to high intensity components of the spectral radiation is limited and for longer exposure times charge accumulation in elements of the detector due to feeble intensity components of the spectral radiation is increased, (iv) obtaining a separate data set for each exposure time such that measurement data at a wavelength at which the intensity is high is obtainable from a data set collected for a short duration exposure time and measurement data at a wavelength at which the intensity is low is obtainable from a data set collected for a relatively long duration exposure time, and (v) extracting spectrochemical information about the sample from measurement data selected from different ones of the separate data sets.

The invention also provides, in a second aspect, spectroscopy apparatus for spectrochemical analysis of a sample comprising a spectroscopic radiation source and a system for interacting the radiation source and a sample for providing spectral radiation of the sample, an optical spectrometric system including a polychromator and a multi-element solid state detector for providing intensity measurements of the spectral radiation as a function of wavelength and means for reading a plurality of elements of the detector to provide said intensity measurements, and a device that is operable on application of an electrical signal thereto to prevent or to allow transmission of the spectral radiation to the detector, wherein the device is selectively operable for the detector to be exposed to the spectral radiation for a plurality of exposure times of varying duration.

The radiation source may be adapted to receive a representative portion of an analytical sample and to heat this portion to a temperature sufficient to decompose it and to excite spectrochemical emission of light from molecules, atoms or ions resulting from the decomposed portion, for example as in atomic emission spectrometry. Alternatively light from the radiation source may be passed through a decomposed sample portion and its absorption at particular wavelengths measured, for example as in atomic absorption spectrophotometry. Other techniques encompassed by the invention include passage of radiation through a suitably presented sample and measurement of its absorption at particular wavelengths (for example as in ultra-violet-visible absorption spectrometry, or infrared absorption spectrophotometry), or measurement of emitted light at particular wavelengths (for example as in fluorescence spectrophotometry). The wording herein of interacting a radiation (or light) source and a sample for providing "spectral radiation (or light) of the sample" is intended to encompass all of these and other similar spectrochemical analysis techniques involving the measurement of the intensity of resultant radiation as a function of wavelength.

The detector of the second aspect of the invention consists of an array of detection elements that can be read by passing charge from one optically sensitive detection element (or pixel) to the immediately adjacent optically sensitive detection element (or pixel) in the same column while the detector is not exposed to light. Means are provided for minimising the spread of charge from any given pixel to all adjacent pixels. This reduces the detrimental effects of any spread of charge ('blooming') that result from the exposure of a pixel to excessively intense radiation. Preferably the detector is oriented in such a way that the effect of blooming is restricted to pixels that would be exposed to radiation in the same spectral order as the radiation that caused the blooming. Any blooming that may occur is thus manifested as a spreading of an intense spectral line rather than as an unexpected increase in intensity at a remote wavelength. Preferably the detector is of the type known as a 'megapixel array', having a large number of pixels (nominally 1 million) and preferably the optical system is so configured that when an optical spectrum is projected onto the detector by said optical system there is a plurality of pixels in the area of the detector that receives each spectral feature of interest (for example each atomic or ionic emission line in an emission spectrometric measurement). In the manufacturing process of array detectors, it is to be expected that a variable number of pixels in each detector will be defective. If there be a plurality of pixels in the area upon which any specific emission line is imaged, a detector will be functional even if one of said plurality of pixels at said position is defective. This means that the yield of useful detectors from the detector manufacturing process is greater than it would be if, for example, only one pixel were provided at each position at which a spectral line were imaged. This greater yield of useful detectors has the effect of reducing the unit cost of the detectors. Preferably too the detector is back-thinned and back illuminated, as described for example in 'Charge Transfer Devices in Spectroscopy', J. V. Sweedler, K. L. Ratslaff and M. B. Denton, eds., VCH Publishers, Inc., New York, 1994, to provide efficient detection of ultraviolet light. Preferably the detector is responsive to light having wavelengths ranging from the far ultraviolet (for example 175 nm) to the far red end of the optical spectrum (for example 785 nm).

To allow the accurate measurement of the wide range of intensities of radiation that are required for the spectrochemical analysis of analytical samples, each reading of the intensity of light at the wavelengths required for a spectrochemical measurement consists of a sequence of exposures of varying duration. This is to ensure that each reading includes at least one exposure in which the amount of charge accumulated at each wavelength of interest is neither too little nor too great. The duration of each exposure of the detector is controlled by the period of time for which an optical shutter or other equivalent device is maintained in a state that allows radiation from the source to fall on the detector.

Preferably, to increase further the range of intensities of radiation that can be measured, at least one exposure is made with an optical attenuator placed between the source and the detector. The use of an attenuator is desirable in that it permits longer exposure times to be used for the measurement of intense radiation. Long exposure times are advantageous in that they result in the averaging out of any periodic variations in the intensity of incident radiation that may be introduced, for example, by the action of a pump used to transport a liquid sample into a radiation (i.e. an excitation) source such as an electrical plasma.

The set of data from each exposure is stored separately. Measurement at a wavelength at which the intensity of radiation is high is obtained from a data set collected with a relatively short measurement time and with the optical attenuator placed between the source and the detector. Measurement at a wavelength at which there is only a low intensity of radiation is obtained from a data set collected with a relatively long exposure time and without the optical attenuator between the source and the detector. Measurements at wavelengths at which there is an intermediate intensity of radiation is obtained from data sets having intermediate exposure times. The selection of appropriate data is done automatically, using pre-set criteria to choose data corresponding to an appropriate amount of charge accumulation.

Thus the method of the invention includes exposing the detector to radiation from the light (radiation) source for a plurality of exposure times of varying duration, said duration being established by the period of time for which the optical shutter or other equivalent selectable light-excluding means allows light from the source to fall on the detector. Preferably at least one such exposure is made with an optical attenuator, which preferably reduces the transmission of light by factors of 10 to 100, placed between the light source and the detector. Data from each exposure is stored and analysed and only data corresponding to an appropriate level of charge accumulation is taken for further processing to extract spectrochemical information about the sample.

For a better understanding of the invention and to show how it may be carried into effect, embodiments thereof will now be described, by way of non-limiting example only, with reference to the accompanying drawings.

DETAILED DESCRIPTION

Figure 1:
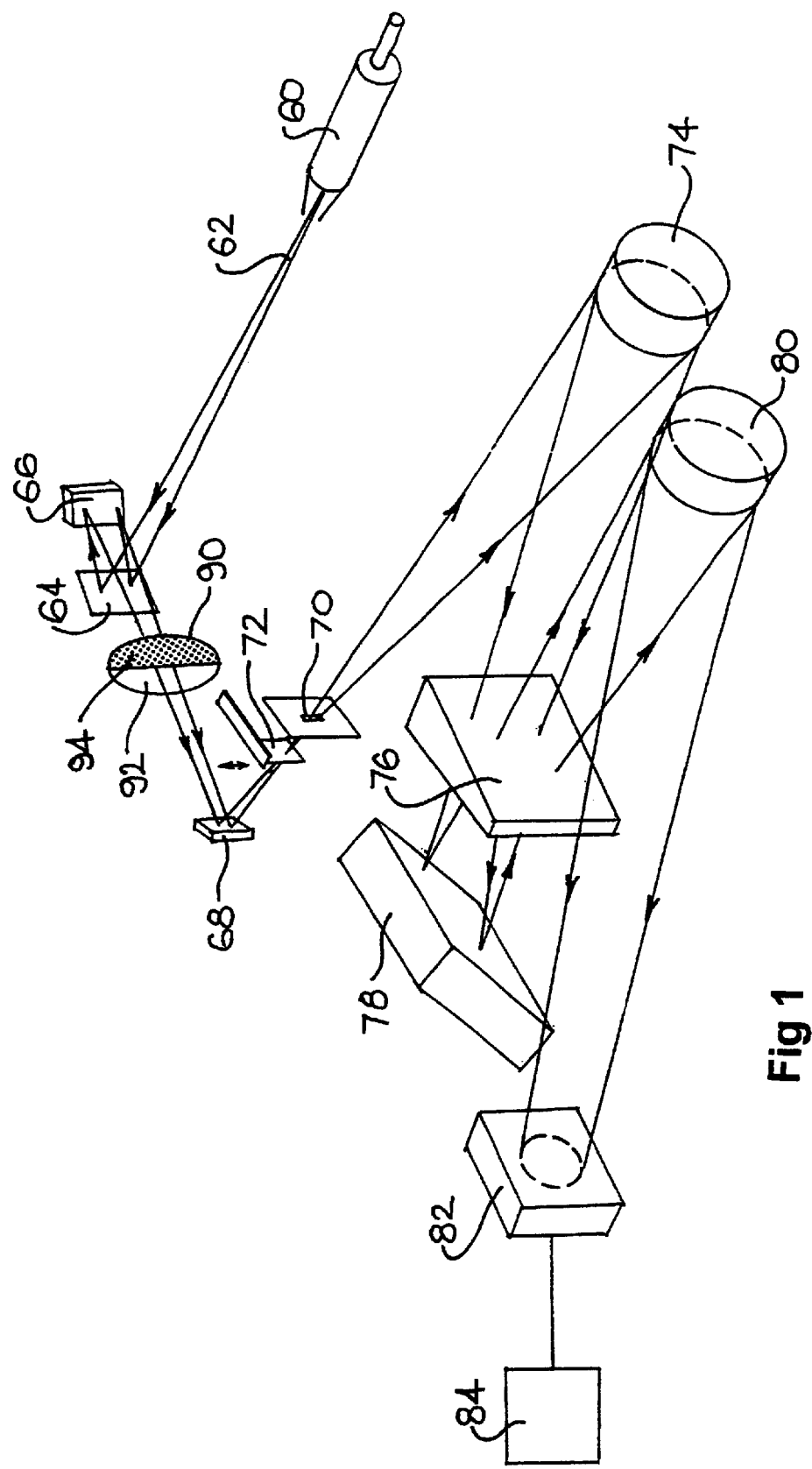
FIG. 1 is a schematic diagram of spectroscopy apparatus according to an embodiment of the invention, being an optical emission spectrometer.

An example of spectroscopy apparatus according to the invention, namely an optical emission spectrometer as illustrated by FIG. 1, comprises a spectroscopic light source 60 which emits spectral light 62 of a sample. Light source 60 in a preferred embodiment is an inductively coupled plasma but may be any other spectroscopic light source adapted to emitting light of spectroscopic interest (i.e. spectral light of a sample).

For the purpose of obtaining information about the chemical composition of an analytical sample, a representative portion of the sample is introduced into spectroscopic light source 60 by means known to those skilled in the art, and is therein caused to emit light 62 that contains information indicative of the chemical composition of the sample. By way of example, if spectroscopic light source 60 is an inductively coupled plasma torch, the representative portion of the sample can be introduced into the inductively coupled plasma torch as an aerosol generated by known nebulising means (not shown) from a solution wherein a known quantity of the sample has been dissolved. The aerosol enters a radio frequency plasma sustained in argon or other appropriate gas flowing in the torch by radiofrequency induction means (not shown). At the high temperatures prevailing in the plasma the aerosol is converted by the action of heat into atoms and ions. Electrons in the atoms and ions are raised to excited energy states by interaction with the hot plasma and, on returning to their stable energy states, emit light having wavelengths characteristic of each chemical element that gave rise to any of the atoms or ions. The intensity of light at the specific wavelengths characteristic of a chemical element is directly related to the number of atoms or ions of that element present in the plasma and thus to the concentration of the chemical element in the analytical sample. Measurements of light intensity at specific wavelengths are converted to measurements of the concentration of specific chemical elements of interest by reference to measurements made when samples having known concentrations of said chemical elements are subjected to the measurement process.

The rest of the apparatus shown in FIG. 1 is for the purposes of separating spectral light 62 emitted by spectroscopic source 60 into its constituent wavelengths and measuring the intensity of the light at wavelengths of interest, such measurement being performed simultaneously at all wavelengths. The basic optical arrangement shown in FIG. 1 is an optical spectrometer based on an echelle polychromator. A similar optical spectrometer was used by Zander et al in U.S. Pat. No. 5,596,407.

The present invention in one embodiment involves the use of a shutter 72, an attenuator 90 and light detector 82 to achieve accurate measurement of light 62 at a plurality of wavelengths and of a wide range of intensities (up to 7 decades for wavelengths<200 nm) at a high speed.

Those skilled in the art will appreciate that the components shown are rigidly and precisely mounted in an opaque housing (not shown) and that an aperture (not shown) preferably including a window (not shown) made of a material transparent to light of all wavelengths of interest is provided to allow spectral light 62 to enter the opaque housing and fall on a mirror 64. Furthermore, those skilled in the art will also appreciate that the opaque housing may advantageously be flushed with a gas transparent to wavelengths of interest, particularly if these wavelengths lie in the far ultra violet region of the spectrum (<200 nm) and are consequently subject to absorption by oxygen. Those skilled in the art will also understand that it is advantageous to maintain the entire optical system at a fixed and stable temperature in order that the spatial locations and orientations of optical components remain as far as possible constant and reproducible during the measurement process. Means for providing such a fixed and stable temperature are known in the art.

Spectral light 62 emitted by spectroscopic light source 60 falls on mirror 64. Advantageously mirror 62 can be provided with adjustment means (not shown) so that light can be selected according to its spatial origin within spectroscopic light source 60. Spectral light 62 is reflected from mirror 64 onto a focussing mirror 66. The spectral light 62 then passes through attenuator 90. Attenuator 90 is provided with segments 92 and 94 of different transparency to spectral light 62 at wavelengths of interest. Attenuator 90 is also provided with means (not shown) by which it can be selectively placed in a first position in which segment 94 is in the path of light 62 and in a second position in which segment 92 intercepts light 62. For illustrative purposes two such segments of different transparency are shown. Segment 92 is fully transmissive of incident light, while segment 94 is only partially transmissive. By selectively placing segment 92 in the path of the light 62, the light is passed without attenuation. By selectively placing segment 94 in the path of the light 62, the light may be reproducibly attenuated. Although only two attenuating segments 92, 94 have been illustrated, it is to be understood that a more than two attenuating segments can be provided in attenuator 90 so as to provide means of selectively and reproducibly attenuating light 62 to a plurality of degrees of attenuation.

The spectral light 62 then strikes a folding mirror 68 and is thereby directed onto aperture 70 of a polychromator, onto which it is focused by the action of focussing mirror 66. A shutter device 72 is so located with respect to aperture 70 that the shutter 72 can selectively be moved to a first position in which it obstructs spectral light 62 or to a second position in which spectral light 62 passes without obstruction.

The shutter device 72 is preferably a cantilever bimorph as is disclosed in the Applicant's International Application No. 09/958,448 entitled "Optical Shutter for Spectroscopy Instrument" filed concurrently with the present application, the disclosure of which is to be considered as incorporated herein by this cross-reference.

When shutter device 72 is in the second position the spectral light 62 passes through aperture 70 and falls on a first polychromator focussing mirror 74 which focuses the spectral light 62 through an order-separating prism 76 and onto an echelle grating 78. Light reflected from echelle grating 78 has been spatially separated in a first direction according to wavelength but a plurality of spectral orders are spatially superimposed, as is known to those skilled in the art. On passing through order-separating prism 76 the spectral light 62 is spatially separated in a second direction according to wavelength. The light 62 then strikes a second polychromator focussing mirror 80 which focuses it onto the array detector 82. An image of aperture 70 is formed on array detector 82 at a spatial position that is determined by the wavelength of the light. Array detector 82 is provided with a large plurality of light-detecting elements (pixels) that convert, by known means, incident light intensity into an electrical charge proportional to the intensity of the incident light.

Measurement of the electric charges generated at specific spatial positions on array detector 82 by means 84 for serially reading a plurality of elements of the detector 82 (which means is known) thus provides a measurement of the intensities of light of specific wavelengths. Such intensity measurements are converted to measurements of the concentration of specific chemical elements by reference to measurements made when samples having known concentrations of said chemical elements are subjected to the measuring process.

Figure 2:
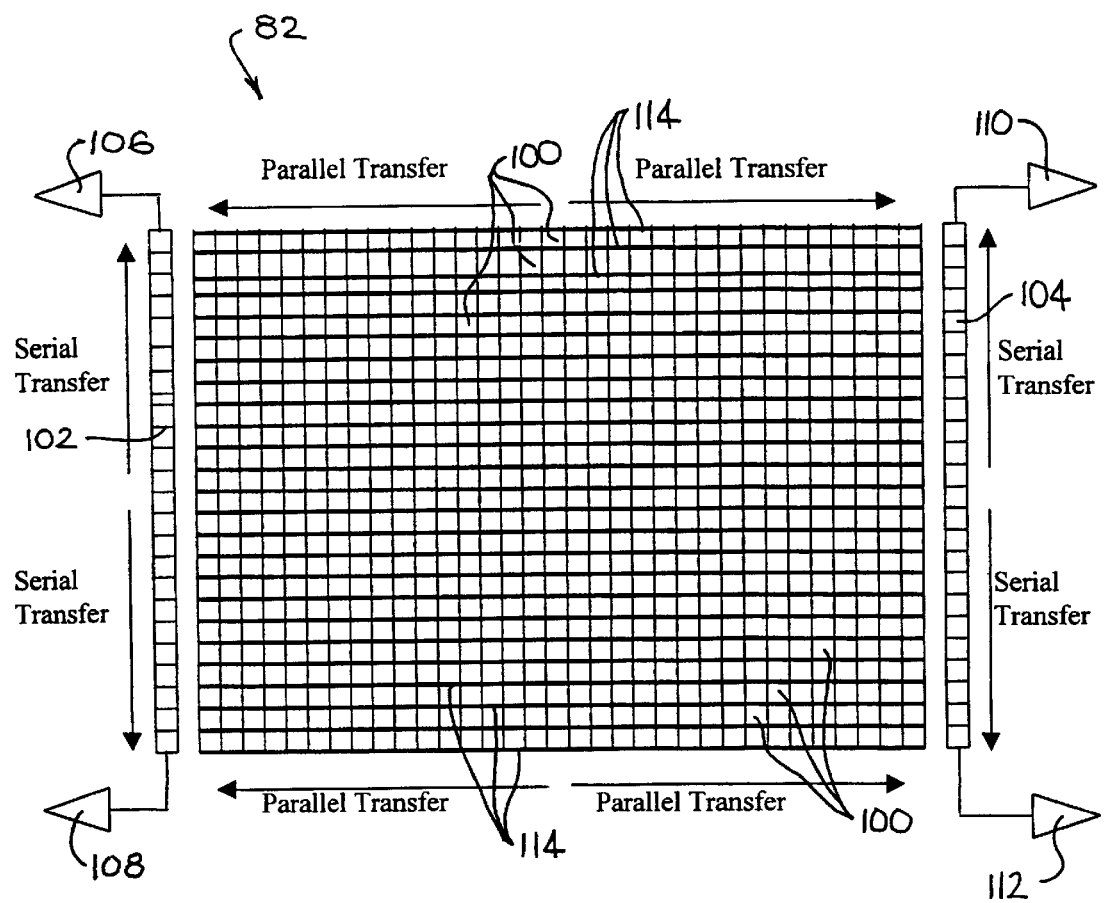
FIG. 2 is a schematic diagram of a preferred multi-element solid state detector for use in the apparatus of FIG. 1.

A preferred array detector 82 is a charge-coupled device (CCD) array detector, as shown schematically in FIG. 2. The CCD array detector comprises an array of elements or pixels 100 arranged in a rectilinear grid, two serial transfer registers 102, 104, and four output amplifiers 106, 108, 110, 112. Light impinging on each element or pixel 100 produces an accumulation of electrical charge in the pixel. The CCD array is preferably cooled to a low temperature, for example −20 degrees Celsius, to reduce the noise that is associated with dark current.

The pixel charges in the CCD array are moved from one place to another in the array by a process called "clocking". This process involves the sequential application of different voltages to specific regions of the array detector 82. Pixel charges are read out from the array detector 82 by transferring charges from pixels 100 into immediately adjacent pixels 100 within the same column (columns are shown horizontally in FIG. 2). Pixel charges cannot be transferred to adjacent columns because of specially doped regions known as "channel stops" 114 separating the columns.

The process for reading out all pixels 100 is:
1. Clear any charge from the serial transfer registers 102, 104 by clocking all transfer register pixels out to the output amplifiers.
2. Transfer one complete row of pixels' charges in parallel from the optically sensitive pixel array 100 into the serial transfer registers 102, 104. As this row of charges is transferred, all other pixel charges are transferred one row towards the serial transfer registers 102, 104 (rows are shown vertically in FIG. 2).
3. Read out each pixel in the serial transfer registers 102, 104 by sequentially clocking the charges in a register towards the respective output amplifier 106–112. Each charge moved to an output amplifier 106–112 is converted to a digital value and transferred to storage memory.
4. Repeat from step 2 until all rows of pixels 100 have been read.

CCD array detectors can be designed to have any number of transfer registers and output amplifiers. The use of four amplifiers 106–112 and two serial transfer registers 102, 104 in the preferred embodiment provides an increase in the speed of readout by a factor of four (4) over a single amplifier design.

As each charge packet is moved to an output amplifier 106–112 it is sampled using correlated double sampling to remove switching noise, filtered to reduce output amplifier noise and converted to a digital value using a 16 bit analog to digital converter.

Figure 3:
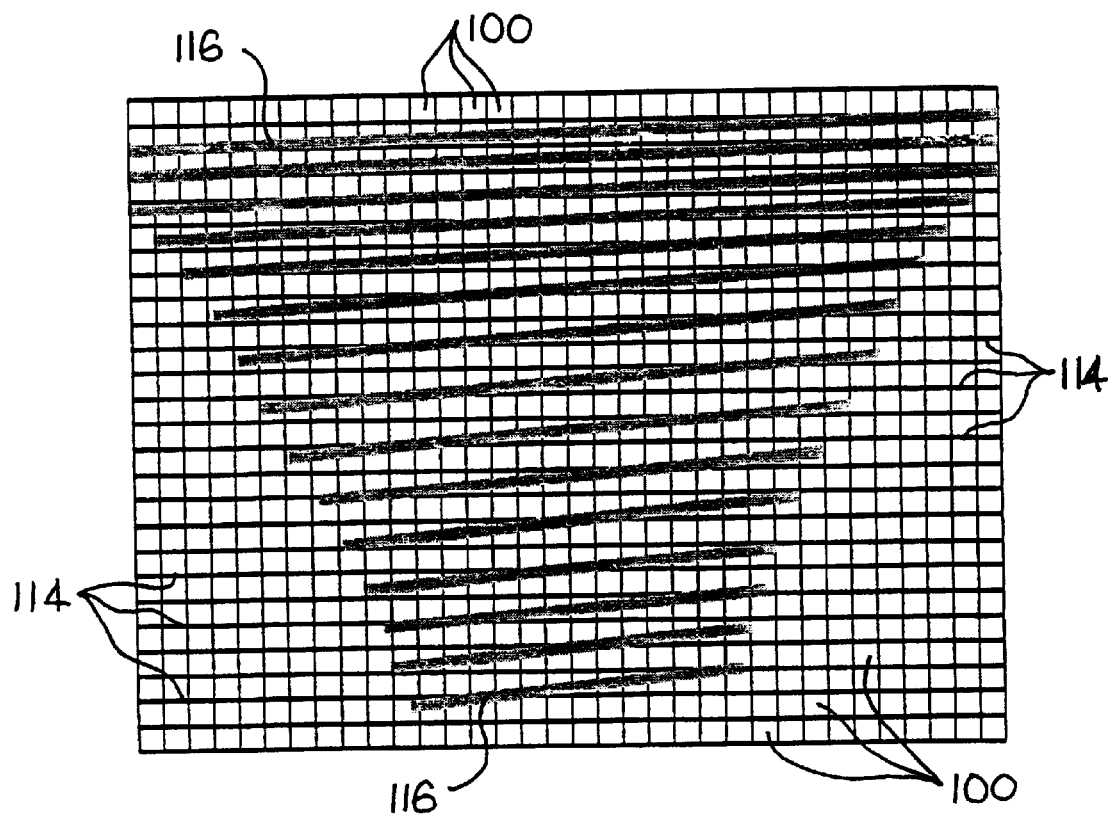
FIG. 3 is a schematic diagram of an echellogram on the array detector of FIG. 2.

Referring now to FIG. 3, light impinging on the array detector 82 falls in a pattern 116 (called an "echellogram") that results from the spatial separation of spectral light 62 according to wavelength produced by diffraction of the light by the echelle grating 78 and dispersion of the light by order-sorting prism 76. The orientation of the detector 82 is so set that the spectral orders in the echellogram 116 are approximately aligned with the channel stops 114.

The pixels 100 in the CCD detector 82 have a limited capacity to store charge. When exposed to radiation a pixel will fill with charge and excess charge will overflow into adjacent pixels. This process is referred to as 'blooming'. Spectra generated from the preferred spectroscopic light source 60 (an inductively coupled plasma) can be expected to contain emission lines having sufficiently intense radiation to fill a pixel 100 within 1 millisecond.

The pixels 100 in the CCD detector 82 have a limited capacity to store charge. When exposed to radiation a pixel will fill with charge and excess charge will overflow into adjacent pixels. This process is referred to as 'blooming'. Spectra generated from the preferred spectroscopic light source 60 (an inductively coupled plasma) can be expected to contain emission lines having sufficiently intense radiation to fill a pixel 100 within 1 millisecond.

It is known in the art that antiblooming structures may be built into each pixel to prevent blooming, but these structures can be expected to result in reduced quantum efficiency and to reduce the amount of charge that can be stored in each pixel ('full well capacity'). This is because the antiblooming structures occupy space that could otherwise be occupied by means to collect aditional light and to store additional charge. To overcome these disadvantages, it is preferable to use the technique known as 'clocked antiblooming' or 'clocked recombination antiblooming' that is discussed for example in 'Scientific Charge-Coupled Devices', J. R. Janesick, SPIE Press, Bellingham, Wash., 2001, ISBN0-8194-3698-4, pp. 293-300. In the detector used in a preferred embodiment the CCD and its associated coperating parameters have been optimised to permit very efficient clocked antiblooming, with good full well capacity and low dark current.

Most solid state two dimensional area image sensors are designed for the detection of visible light, and are relatively insensitive to ultraviolet (UV) light, that is, to light having wavelengths below 400 nm. This is a serious disadvantage for spectrochemical application, because a significant number of spectral features of interest occur in the UV. The poor sensitivity is due to absorption and reflection losses incurred by structures at the surface of the detector. There are a number of known means to improve UV sensitivity, each of which has inherent advantages and disadvantages, as discussed for example in 'Scientific Charge-Coupled Devices', J. R. Janesick, SPIE Press , Bellingham, Wash., 2001, ISBN0-8194-3698-4, pp. 178-287. A process has been employed in the manufacture of the detector used in the preferred embodiment of the invention, to significantly improve sensitivity to UV and visible wavelengths, whereby the material underlying the epitaxially-deposited structure of the detector is etched back to the level of the epitaxy, and then oxidized and coated with an antireflective coating. This process is known as back thinning, and a detector that has undergone this process is so mounted as to receive the light to be detected from the direction of the etched substrate. Such a detector is commonly referred to as a 'back-thinned', or 'back-illuminated'. An optimized back-thinned CCD array detector, such as that used in the preferred embodiment of the invention, can be expected provide higher UV sensitivity than the alternative common approaches, as discussed 'Scientific Charge-Coupled Devices', J. R. Janesick, SPIE Press , Bellingham, Wash., 2001, ISBN0-8194-3698-4, pp. 178–287.

If there are areas of especially intense radiation at certain wavelengths, sufficient to generate charge in the detector 82 at a faster rate than can be removed by anti-blooming, the excess charge will fill pixels 100 and cause them to overflow. The excess charge from blooming will preferentially spill into adjacent pixels in the same column rather than cross a channel stop. This results in observed spectral interference at wavelengths adjacent to the intense wavelength. The neighbouring spectral orders are unaffected by interference from blooming.

When the apparatus of this invention is used determining the concentration of specific chemical elements in analytical samples by optical emission spectrometry, for example, it is desirable that said elements should be detectable at low concentrations such as, for example, only a few micrograms per liter. It is also desirable that the apparatus should be able to measure concentrations of specific chemical elements present in said samples at concentrations of several hundred milligrams per liter, for example.

To unambiguously detect concentrations of specific chemical elements at concentrations of a few micrograms per liter the apparatus must be capable of measuring spectral features (in this example atomic or ionic emission lines) having intensities so low that a pixel will not saturate even when continuously exposed to the radiation of such spectral features for 10 seconds, for example. Those skilled in the art will appreciate that when intensities of such a low level are measured using short exposure times such as 1 millisecond, for example, the measured signals are completely dominated by 'shot noise', which is the variability in the signal arising from the randomness inherent in the generation of electrons by light. Such noisy signals are not useable for determining concentrations of the chemical elements of interest. Those skilled in the art will appreciate that the relative shot noise for a given intensity of radiation reduces in proportion to the square root of the exposure time. For the measurement of low intensities, it is therefore advantageous to use long exposure times, for example 10 seconds.

A chemical element that is present at relatively high concentrations in an analytical sample will produce a relatively intense spectral feature at the detector. As discussed hereinbefore, however, spectral features having a relatively high intensity will cause the corresponding pixels of the detector to saturate in a relatively short time. Consequently no useful measurements of relatively high intensity spectral features are possible at the long exposure times that are necessary to obtain useful information from relatively weak spectral features. To make useful measurements of the concentrations of chemical elements of interest over the wide range of concentrations found in analytical samples the apparatus must be able to measure spectral features having a wide range of intensities. To do this the apparatus must employ a plurality of exposure times, collecting a data set from each exposure. Certain groups of pixels within each data set are selected to measure particular spectral features. The apparatus uses a selection of different exposure times chosen to cover the range of expected signal intensities for each spectral feature. Furthermore, for the measurement of spectral features having intensities that would saturate the corresponding pixels even at the shortest exposure times, an optical attenuator is so placed between the light source and the detector that the intensity of light is reduced to a level that can be usefully measured.

For each exposure time, a selected number of repeated exposures are performed to allow reduction of signal noise by averaging. Examples of exposure times used in a preferred embodiment of the invention are shown below.

| Exposure time (milliseconds) | Number of exposures | Attenuator Used |
|---|---|---|
| 10 | 2 | Yes |
| 100 | 4 | Yes |
| 500 | 2 | Yes |
| 100 | 4 | No |

-continued

| Exposure time (milliseconds) | Number of exposures | Attenuator Used |
|---|---|---|
| 1000 | 2 | No |
| 10000 | 1 | No |

The sequence of operations performed to collect each one of the sets of data is:
1. select the required attenuator position
2. clear the detector device of all accumulated charge
3. open the shutter
4. wait for the required exposure time
5. close the shutter
6. read out and store data from the detector When the data sets have been collected using the above sequence for each exposure, the data sets are processed to derive spectral feature intensity data for each chemical element of interest. Each spectral feature of interest is identified from the known relationship between the spatial position of each pixel on the detector and the wavelength that is detectable by that pixel. This relationship is established initially by the optical design of the spectrometer and the specific relationship for a particular spectrometer is determined by reference to calibration samples of known composition that provide spectral features at known wavelengths.

The procedure for processing data sets to derive spectral feature intensity data for each chemical element of interest is as follows:
1. Select a spectral feature of interest
2. Select the longest exposure time that does not result in saturation of any data within that spectral feature for any of the data sets using that exposure time
3. Average the data sets collected using the selected exposure time
4. If data was collected with the attenuator in the light path, correct the pixel intensity data using attenuation factors from the attenuator calibration.
5. Derive spectral feature intensity values from the selected, averaged data sets
6. Repeat from 1 until all spectral features have been processed.

The speed of measurement can be enhanced by omitting to convert selected rows of pixels or groups of pixels within a row if the information contained therein is not required. If conversion is restricted to only those pixels that provide information about the spectral features of interest the total reading time is thereby reduced.

The observed magnitude of signals measured depends directly on the amount of time the detector is exposed to illuminating radiation. For this reason, the shutter timing accuracy and repeatability directly affect the measurement accuracy and repeatability. A preferred embodiment of the invention employs a shutter that can switch in less than 5 milliseconds with a repeatability of better than 100 microseconds. To maintain signal measurement repeatability the minimum exposure time used in the instrument is set at 10 milliseconds. To be able to measure intense radiation that would otherwise saturate the corresponding pixels in the detector in less than 1 millisecond, the apparatus employs an attenuator to reduce intensities by a factor of between 10 and 100.

Both shutter and attenuator need to be calibrated to achieve accurate measurements.

There is a time delay from actuating the shutter until the light path is unblocked, and a different delay from actuating the shutter until the light path is blocked. The difference in these delays represents the timing inaccuracy of the shutter. The shutter calibration measures the size of the timing inaccuracy of the shutter by comparing signal intensities measured using a single long exposure (of about 1 second) with signal intensities measured using many short exposures (each about 10 milliseconds) whose exposure times sum to the same time interval as the long exposure. The timing error is calculated from the equation:

$$\text{timing\_error} = \text{total\_integration\_time} * (1 - \text{intensity\_2}/\text{intensity\_1})/\text{n\_cycles}$$

where
  total_integration_time is the integration time for the long single exposure
  intensity_1 is the intensity measured for the long single exposure
  intensity_2 is the intensity measured from multiple short exposures
  n_cycles is the number of short exposures needed to give an equivalent exposure time to the long exposure.

Since the signal reduction caused by the attenuator directly affects the accuracy of intensity measurements, the attenuator must be calibrated. This is done by measuring spectral features whose peak intensities lie within such a range that they can be reliably measured both with the attenuator in the light path and with the attenuator out of the light path. Since the attenuation factor of the attenuator used in the preferred embodiment has been shown to vary slowly and smoothly with wavelength, a representative number of spectral features covering the whole of the desired wavelength range of the apparatus has been selected for this calibration. The ratio of attenuated intensity to un-attenuated intensity is stored for each selected calibration point. Subsequent measurements made with the attenuator in the light path are corrected by dividing measured intensity by the stored attenuation ratio for the measured wavelength. Mathematical interpolation is used to calculate attenuation ratios for wavelengths other than those calibrated.

According to the invention, the shutter device 72 is operated by application of an electrical signal to its piezoelectric structure to move the shutter to the first position to prevent the spectral light 62 from reaching the detector 82. This allows a plurality of the elements of the detector 82 to be serially read by the means 84 whilst the detector 82 is shielded from the spectral light 62.

Thus there is described spectroscopy apparatus for spectrochemical analysis of a sample which comprises a radiation or light source 60 for interacting the light source and a sample for providing spectral radiation or light 62 of the sample. The optical spectrometric system of the spectroscopy apparatus includes a polychromator 70, 74–78 and the multielement solid state detector 82. The apparatus also includes means 84 for reading a plurality of the elements of the detector to provide light intensity measurements. The apparatus furthermore includes a device 72 that is operable on application of an electrical serial thereto to prevent or allow transmission of the spectral light 62 to the detector 82, which device 72 is selectively operable for the detector 82 to be exposed to the spectral light 62 for a plurality of exposure times of varying duration.

The invention described herein is susceptible to variations, modifications and/or additions other than those specifically described and it is to be understood that the invention includes all such variations, modifications and/or additions that fall within the scope of the following claims.

What is claimed is:

1. A method for spectrochemical analysis of a sample comprising:
   (i) interacting a representative portion of the sample and a spectroscopic radiation source to produce spectral radiation of the sample,
   (ii) measuring the intensity of the spectral radiation as a function of wavelength by passing the spectral radiation through a polychromator onto a multi-element solid state detector comprising a plurality of pixels and reading said plurality of pixels of the detector, including:
   (iii) exposing all said pixels of the detector to the spectral radiation for plurality of common exposure times of varying duration whereby for short exposure times charge accumulation in those pixels of the detector coincident with high intensity components of the spectral radiation is limited and for longer exposure times charge accumulation in pixels of the detector coincident with feeble intensity components of the spectral radiation is increased,
   (iv) obtaining a separate data set for each exposure time such that measurement data at a wavelength at which the intensity is high is obtainable from a data set collected for short duration exposure time and measurement data at a wavelength at which the intensity is low is obtainable from a data set collected for a relatively long duration exposure time, and
   (v) extracting spectrochemical information about the sample from measurement data selected from different ones of the separate data sets.

2. A method as claimed in claim 1 including serially reading the plurality of pixels of the detector to obtain a data set while not exposing the detector to the spectral radiation.

3. A method as claimed in claim 1 including for short exposure times attenuating the spectral radiation on the detector to thereby reduce the intensity 30 of high intensity components of that spectral radiation.

4. Spectroscopy apparatus for spectrochemical analysis of sample comprising:
   a spectroscopic radiation source and a system for interacting the radiation source and a sample for providing spectral radiation of the sample,
   an optical spectrometric system including a polychromator and a multi-element solid state detector comprising a plurality of pixels for providing intensity measurements of the spectral radiation as a function of wavelength and means for reading said plurality of pixels of the detector to provide said intensity measurements,
   a device that is operable on application of an electrical signal thereto to prevent or to allow transmission of the spectral radiation to the detector, wherein the device is selectively operable for the detector to be exposed to the spectral radiation for a plurality of exposure times of varying duration,
   storage apparatus for retaining data acquired at each of said plurality of exposure times, and
   said detector further comprising means for limiting the flow into adjacent pixels of excessive charge from any pixel exposed to intense radiation and said detector is oriented with the optical spectrometric system such that any flow of excessive charge from pixels of the detector into adjacent pixels is restricted to pixels that are exposed to spectral radiation in the same spectra order as the spectral radiation causing the excessive charge.

5. Spectroscopy apparatus as claimed in claim 4 including control means for automatically operating said device using pre-determined criteria to provide said plurality of exposure times of varying duration.

6. Spectroscopy apparatus as claimed in claim 4 wherein the means for reading a plurality of pixels of the detector is operative for serially reading a plurality of the pixels of the detector and said device is operative for the plurality of detector elements to be serially read while the detector is shielded from the spectral radiation.

7. Spectroscopy apparatus as claimed in claim 4 wherein the means for limiting the flow of excessive charge comprise regions of the detector between columns of its pixels which are doped to prevent transfer of charge to elements in adjacent rows of the elements.

8. Spectroscopy apparatus as claimed in claim 4 including an optical attenuator located between the radiation source and the detector for attenuating high intensity spectral radiation to which the detector may be exposed.

9. Spectroscopy apparatus as claimed in claim 8 wherein the optical attenuator reduces the transmission of radiation by a factor of between 10 to 100.

10. Spectroscopy apparatus as claimed in claim 4 wherein said device is a shutter which includes a piezoelectric actuator.

11. Spectroscopy apparatus as claimed in claim 10 wherein the piezoelectric actuator is a bimorph.

12. Spectroscopy apparatus as claimed in claim 11 wherein the bimorph is mounted as a cantilever having a free end which on application of the electrical signal moves along an arc for preventing or allowing transmission of the spectral radiation to the detector.

* * * * *